United States Patent [19]
Kaltenekker et al.

[11] 4,300,398
[45] Nov. 17, 1981

[54] APPARATUS FOR MEASURING DEFLECTION OF A BLADE UPON APPLICATION OF FORCE THERETO

[75] Inventors: Bela Kaltenekker; William L. Loofbourrow, both of Healdsburg, Calif.

[73] Assignee: Fairchild Camera & Instr. Corp., Mountain View, Calif.

[21] Appl. No.: 99,963

[22] Filed: Dec. 3, 1979

[51] Int. Cl.³ ............................................. G01N 3/20
[52] U.S. Cl. ................................... 73/849; 73/862.45
[58] Field of Search ...................... 73/849, 144, 862.39, 73/862.45

[56] References Cited
U.S. PATENT DOCUMENTS 3,304,770  2/1967  Dixon ...................................... 73/849
3,839,908  10/1974 Casper .................................... 73/144
4,213,334  7/1980  Wikoff ..................................... 73/144

Primary Examiner—Anthony V. Ciarlante
Attorney, Agent, or Firm—Paul J. Winters; Theodore Scott Park; Kevin McMahon

[57] ABSTRACT

The present apparatus includes a base and a table movably mounted thereto, further including a body secured to the table and a rod movably mounted to the body. The rod is brought into contact with a member such as a saw blade, and the table and body are moved toward the blade a chosen distance, the rod being moved relative to the body a certain distance corresponding to a certain increase in force being applied to the blade by the rod. For a given increase in force applied to the blade, the movement of the rod relative to the body can be compared to the movement of the table relative to the base to determine deflection of the blade for application of that increase in force thereto.

5 Claims, 4 Drawing Figures

APPARATUS FOR MEASURING DEFLECTION OF A BLADE UPON APPLICATION OF FORCE THERETO

BACKGROUND OF THE INVENTION

This invention relates to measuring apparatus, and more particularly to apparatus for measuring the deflection of a member such as a saw blade upon a given increase in force being applied thereto.

In the slicing of an elongated, generally cylindrical silicon ingot into individual wafers, it is well known to provide a rotary saw blade having a central opening defined by a circular inner edge, that edge actually being the cutting edge of the saw blade. The ingot is positioned through the opening, the saw blade is rotated, and the saw blade is further moved generally laterally of the longitudinal axis of the ingot so that the cutting edge contacts and cuts through and across the ingot.

It is to be understood that proper blade tension is of the utmost importance during the slicing operation. Toward this end, the blade should be highly tensioned, yet is must be understood that such a blade has a yield point, i.e., that point beyond which further force applied to the blade so as to increase blade tension actually permanently stretches the material. It has been found highly advantageous to increase such force to a point just short of that yield point. This results in a very high tension of the blade, but without any permanent deformation thereof.

Heretofore, a judgment as to the blade tension has been made by the operator of the apparatus increasing the tension thereof, and then judging by manual contact with the blade the degree of tension of the blade. Obviously such a system presents certain problems, due to the relatively inexact nature of the measurement.

SUMMARY OF THE INVENTION

It is accordingly an object of this invention to provide apparatus for determining the tension on a member such as a rotary saw blade through measurement of deflection of a portion of that blade upon a given increase in force applied thereto.

It is a further object of this invention to provide a method of determining tension of a member such as a rotary saw blade by measuring deflection of a portion of that blade upon a given increase in force applied thereto.

Broadly stated, the apparatus for measuring deflection of a member upon an increase in force applied thereto comprises a base, and a table movably mounted to the base so as to be movable in first and second opposite directions relative thereto. Means are included for moving the table relative to the base a chosen distance in the first direction. A body is secured to the table so as to be movable therewith, and a rod is movably mounted to the body so as to be movable in one and the other opposite directions relative thereto, which generally correspond to the first and second opposite directions. Further included are resilient spring means operatively interconnecting the body and rod, against which the rod is movable in the other direction, a given force applied to the rod in the other direction corresponding to a certain movement of the rod relative to the body in the other direction. Further included are indicator means operatively connected with the rod for indicating the amount of force being applied to the rod urging the rod in the second direction.

Broadly stated, the invention further comprises a method of measuring deflection of a member upon an increase in force applied thereto, comprising providing an assembly comprising a body, and a rod movably mounted to the body so as to be movable in one and the other opposite directions relative thereto, resilient spring means operatively interconnecting the body and rod, against which the rod is movable in the other direction, a given force applied to the rod in the other direction corresponding to a certain movement of the rod urging the rod in the other direction, and indicator means for indicating the amount of force being applied to the rod urging the rod in the other direction, the method further comprising bringing the rod into contact with the member with a given amount of force applied by the member to the rod in the other direction. The method further comprises moving the body a certain distance toward the member so that the member applies increasing force to the rod until a chosen force is achieved. The method further comprises moving the body a certain distance toward the member so that the member applies increasing force to the rod until a chosen force is achieved. The method further comprises noting the distance the rod has moved relative to the body toward the member, noting the distance the body has been moved toward the member, and subtracting the distance the rod has moved relative to the body from the distance the body has been moved toward the member.

BRIEF DESCRIPTION OF THE DRAWINGS

These and other objects of the invention will become apparent from a study of the following specification and drawings in which.

DESCRIPTION OF THE PREFERRED EMBODIMENT

Figure 1:
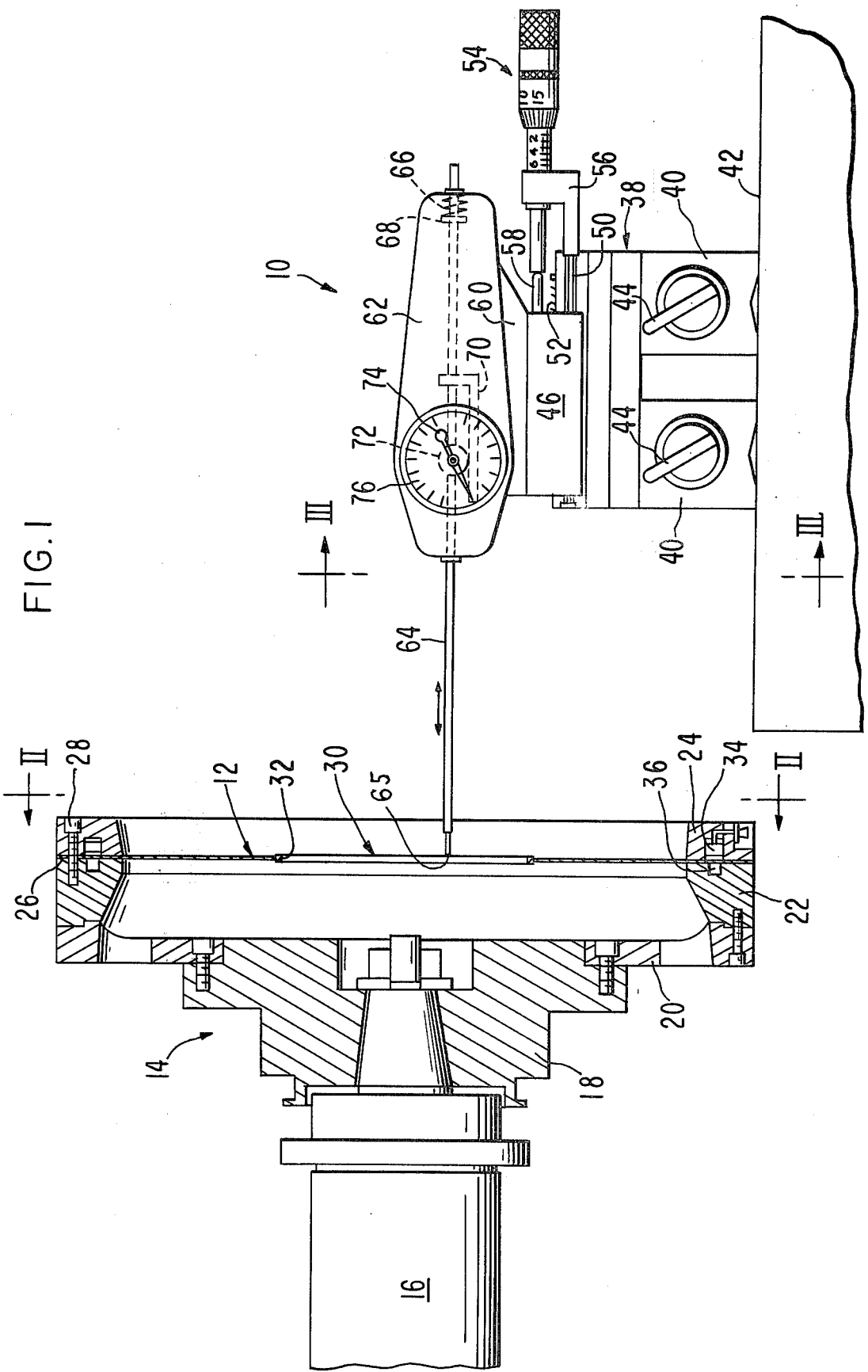
FIG. 1 is an elevational view of the apparatus as used.
Figure 2:
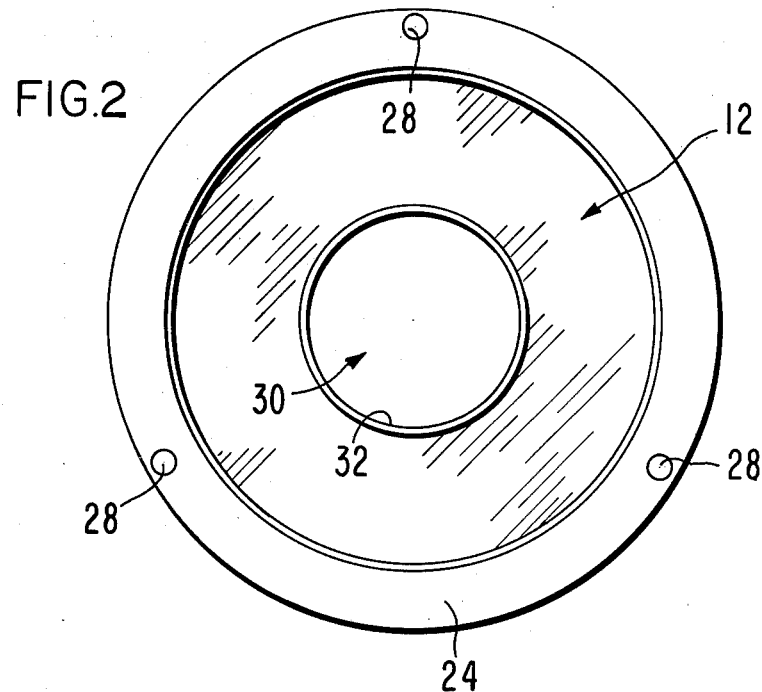
FIG. 2 is a view taken along the line II—II of FIG. 1.

Shown in FIG. 1 is the overall apparatus 10 for measuring deflection of a blade 12 upon application of an increase in force thereto. The blade 12, as also shown in FIG. 2, is mounted to a carrier 14 which in turn is mounted to a rotary shaft 16. The carrier 14 includes a base portion 18 directly bolted to the end of the shaft, a plate member 20 bolted thereto, a first ring member 22 bolted to the plate member 20, and a second ring member 24 bolted to the first ring member 22. The blade 12, as is well known, is circular, having the outer periphery 26 thereof positioned between the rings, 22, 24, with the bolts 28 passing directly through the blade 12 to hold the blade 12. The blade 12 defines a circular central opening 30, the inner edge 32 thereof defining the cutting edge of the blade 12.

As described generally above, an ingot is disposed through the opening 30, and supported in that position, and the shaft 16 is rotated rapidly and also moved laterally of the longitudinal axis of the shaft 16 so that the blade 12 cuts through the ingot.

As is well known, the blade tension may be varied by pumping pressurized fluid such as oil into annular chamber 34 defined by the ring 28. Such pressure forces the blade 12 to bend slightly into opposite annular chamber 36 defined by the ring 26, thereby increasing the tension on the blade 12, it being understood that a small amount of clearance is provided between the blade 12 and rings 26, 28 to allow such blade 12 to be tensioned.

Figure 4:
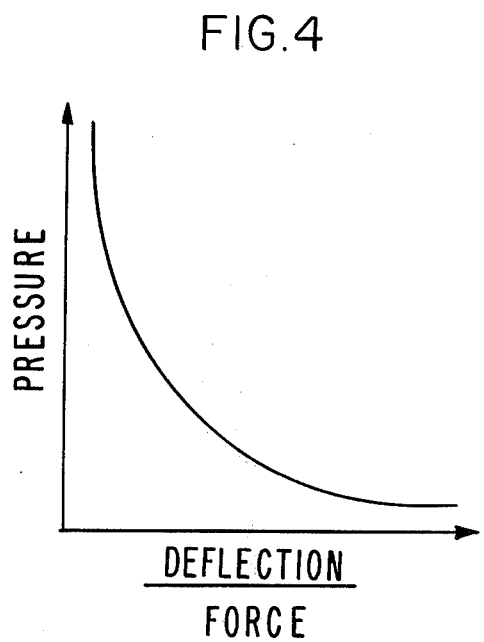
FIG. 4 is a graph of pressure vs. deflection characteristics of the apparatus of FIG. 1.

FIG. 4 shows that as pressure in the chamber 34 is increased, the amount of blade deflection which will take place upon a given increase in force applied at the cutting edge 32 decreases, and as set forth above, it is to be understood that minimal deflection is highly desirable. Yet, as also set forth above, upon sufficient increase of oil pressure in the chamber 34, the yield point of the blade 12 is reached, and the blade 12 will be permanently stretched.

Figure 3:
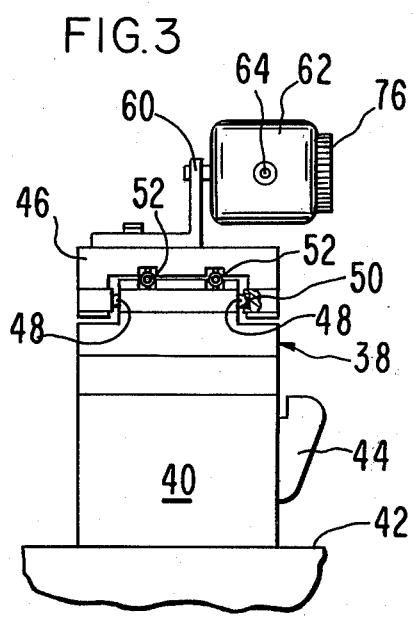
FIG. 3 is a view taken along the line III—III of FIG. 1.

Shown in FIGS. 1 and 3 is the apparatus 10 of the present invention. As shown therein, the apparatus 10 includes a base 38 having a pair of magnet assemblies 40 mounted thereto. The internal magnets thereof may be raised and lowered toward a metal surface 42 by rotation of handles 44, so that the base 38 may be selectively magnetically secured to the metal surface 42. A table 46 is movably mounted to the base 38 by means of rollers 48 rollingly mounted in tracks 50 on the base 38 and table 46. The table 46 is thus movable in first and second opposite directions (i.e. leftward and rightward, FIG. 1), relative to the base 38 and is biased toward its second direction by means of resilient springs 52 interconnecting the table 46 and base 38. The amount of movement of the table 46 relative to the base 38 in either direction can be accurately measured by means of a micrometer apparatus 54 operatively connected with the base 38 and table 46, the micrometer apparatus 54 being mounted to a bracket 56 in turn mounted to the base 38, and contacting a protruding member 58 mounted to the table 46 and movable therewith.

Fixed to the table 46 by means of a bracket 60 so as to be movable therewith is a body 62. The body 62 has disposed therethrough and movable relative thereto an elongated rod 64. The body 62 and rod 64 are positioned so that the rod 64 is movable in one and the other opposite directions relative to the body 62, which directions generally correspond to the first and second opposite directions respectively. A resilient spring 66 within the body 62 is fixed to a collar 68 on the rod 64 and to the body 62. The rod 64 is movable in the other direction against the resilience of the spring 66, a given force applied to the rod 64 in the other direction corresponding to a certain movement of the rod 64 relative to the body 62 in the other direction. A rack 70 is fixed to the rod 64 so as to be movable therewith, the teeth of the rack being in engagement with the teeth of a pinion 72. The pinion 72 is connected by a shaft to a hand 74 which is in turn movable relative to a dial 76 mounted to the body 62.

Prior to description of the use of the apparatus 10 for blade tensioning, it is considered advantageous to describe the operation thereof with the tip 65 of the rod 64 in contact with a rigid member.

Assuming that the tip 65 of the rod 64 is brought into contact with a rigid member and the spring 66 is in its free or uncompressed state, the dial may be set so that the reading of the hand 74 is zero. The micrometer 54 may then be used to move the table 46 and body 62 (FIG. 1) leftward, and since the rigid member is unyielding in this case, the rod 64 will be moved an equal distance relative to the body 46, inwardly thereof. This will continue until a force of, for example, 250 grams is read on the dial 76. Thus, it is known that 250 grams of force are being applied to the member, that the micrometer 54 has moved the table 46 relative to the base 31, for example, 1/10 of an inch, and that the rod 64 has moved relative to the body 62 1/10 of an inch also.

Applying this apparatus 10 to a blade 12 as shown in FIG. 1, it is to be realized that the blade 12 will yield slightly upon application of force thereto by the rod 64. The tip 65 of the rod 64 is brought into contact with the cutting edge 32 of the blade 12, with the spring 66 in a free state so that the reading on the dial 76 is zero. The micrometer reading at this point is noted. The micrometer 54 is then utilized to move the table 46 sufficiently until 250 grams of force are applied by the rod 64 to the blade 12, and conversely by the blade 12 to the rod 64. It is therefore known that the rod 64 has moved 1/10 of an inch relative to the body 62. However, the micrometer change has not been 1/10 of an inch due to the slight bending of the blade 12. In fact, the movement of the table 46 relative to the base 38 will be slightly greater than 1/10 of an inch, the difference being the bending or deflection of the blade 12. Thus, it will be seen that the deflection of the blade 12 upon application of a certain increase in force being applied thereto can be accurately determined.

Once such a figure is established for a certain design of blade 12 for optimum operation thereof, the tensioning of that design of blade 12 can be achieved quickly and in a higher consistent manner.

What is claimed is:

1. Apparatus for measuring deflection of a cutting blade upon an increase in force applied thereto comprising:
    a base;
    a table mounted to the base so as to be movable in first and second opposite directions relative thereto;
    means for moving the table relative to the base a chosen distance in said first direction;
    a body secured to the table so as to be movable therewith;
    a rod mounted to the body so as to be movable in one and the other opposite directions relative thereto, generally corresponding to said first and second opposite directions, the apparatus being positionable to bring a tip of the rod into contact with the cutting blade;
    resilient spring means operatively interconnecting the body and rod, against which the rod is movable in the other direction, a given force applied to the rod in said other direction corresponding to a certain movement of the rod relative to the body in said other direction; and
    indicator means operatively connected with the rod for indicating the amount of force being applied to the rod urging the rod in the other direction.

2. The apparatus of claim 1 and further comprising resilient spring means urging the table in said second direction.

3. The apparatus of claim 2 wherein the means for moving the table relative to the base a chosen distance in said first direction comprises micrometer means operatively connected with the table and base for selectively moving the table relative to the base against the resilient spring means urging the table in said second direction.

4. The apparatus of claim 3 and further comprising magnet means mounted to the base.

5. A method of measuring deflection of a cutting blade upon an increase in force applied thereto comprising:

providing an assembly comprising a body, and a rod movably mounted to the body so as to be movable in one and the other opposite directions relative thereto, resilient spring means operatively interconnecting the body and the rod against which the rod is movable in the other direction, a given force applied to the rod in said other direction corresponding to a certain movement of the rod relative to the body in said other direction, and indicator means for indicating the amount of force being applied to the rod urging the rod in the other direction;

bringing the rod into contact with the cutting blade with a given amount of force applied by the cutting blade to the rod in the other direction;

moving the body a certain distance toward the cutting blade so that the cutting blade applies increasing force to the rod until a chosen force is achieved;

noting the distance the rod has moved relative to the body upon said movement of the body toward the cutting blade;

noting the distance the body has been moved toward the cutting blade; and subtracting the distance the rod has moved relative to the body from the distance the body has been moved toward the cutting blade.

* * * * *